United States Patent
Hamilton et al.

(10) Patent No.: US 9,344,781 B2
(45) Date of Patent: May 17, 2016

(54) COMMUNICATION AND SPEECH ENHANCEMENT SYSTEM

(71) Applicant: Dolores Speech Products, LLC, Wellesley, MA (US)

(72) Inventors: John Hamilton, Wilmington, DE (US); Christopher McDivit, Irvine, CA (US)

(73) Assignee: DOLORES SPEECH PRODUCTS, LLC, Wellesley, MA (US)

( * ) Notice: Subject to any disclaimer, the term of this patent is extended or adjusted under 35 U.S.C. 154(b) by 0 days.

(21) Appl. No.: 14/034,020

(22) Filed: Sep. 23, 2013

(65) Prior Publication Data

US 2014/0093117 A1 Apr. 3, 2014

Related U.S. Application Data

(60) Provisional application No. 61/849,326, filed on Jan. 23, 2013, provisional application No. 61/744,385, filed on Sep. 24, 2012.

(51) Int. Cl.
*H04R 1/00* (2006.01)
*H04R 1/02* (2006.01)
(Continued)

(52) U.S. Cl.
CPC ............... *H04R 1/02* (2013.01); *A61M 16/06* (2013.01); *G10L 13/00* (2013.01); *G10L 21/02* (2013.01); *H04R 1/028* (2013.01); *A61M 16/0468* (2013.01); *A61M 2205/3375* (2013.01); *A61M 2205/3553* (2013.01); *A61M 2205/3592* (2013.01); *A61M 2205/505* (2013.01); *H04R 1/1016* (2013.01); *H04R 1/1066* (2013.01); *H04R 1/1083* (2013.01); *H04R 1/14* (2013.01); *H04R 5/0335* (2013.01); *H04R 2201/107* (2013.01)

(58) Field of Classification Search
CPC .. H04R 1/1066; H04R 1/1016; H04R 5/0335; H04R 1/02; H04R 1/028; H04R 1/1083; H04R 1/14; H04R 2201/107; G10L 21/02; G10L 13/00; A61M 16/0468; A61M 2205/3375; A61M 2205/3592; A61M 2205/505
USPC ........................................................ 381/385
See application file for complete search history.

(56) References Cited

U.S. PATENT DOCUMENTS 2,165,124 A 7/1939 Ballantine et al.
2,950,360 A 8/1960 Duncan
(Continued)

OTHER PUBLICATIONS

International Search Report and Written Opinion from International application No. PCT/US13/00216, dated Nov. 14, 2013.

*Primary Examiner* — Matthew Eason
*Assistant Examiner* — Sean H Nguyen
(74) *Attorney, Agent, or Firm* — Kilpatrick Townsend & Stockton LLP

(57) ABSTRACT

A communication and speech enhancement system featuring a first transducer designed to be temporarily affixed to a human such as a hospital patient to convert the audible vibrations of human speech into an electrical signal. The transducer provides this electrical signal to one or more electronic modules which modify and enhance the signal. The enhanced signal may then be amplified and converted back into audible sound by means of a second transducer. A user of the system controls the electronic modules through a user interface. In an embodiment, one or both of the user interface and second transducer feature smooth surfaces amenable to cleaning and sterilizing with liquid agents.

28 Claims, 1 Drawing Sheet

(51) Int. Cl.
  *G10L 21/02* (2013.01)
  *A61M 16/06* (2006.01)
  *G10L 13/00* (2006.01)
  *H04R 1/10* (2006.01)
  *H04R 5/033* (2006.01)
  *H04R 1/14* (2006.01)
  *A61M 16/04* (2006.01)

(56) References Cited

U.S. PATENT DOCUMENTS

| | | |
|---|---|---|
| 3,180,333 A | 4/1965 | Lewis et al. |
| 3,265,153 A | 8/1966 | Burroughs |
| 3,588,359 A | 6/1971 | Cribb |
| 4,072,831 A | 2/1978 | Joscelyn |
| 4,143,648 A | 3/1979 | Cohen et al. |
| 4,311,872 A | 1/1982 | Davis |
| 4,537,276 A | 8/1985 | Confer |
| 4,607,383 A | 8/1986 | Ingalls |
| 4,736,740 A | 4/1988 | Parker et al. |
| 4,799,263 A | 1/1989 | Banziger et al. |
| 5,163,093 A | 11/1992 | Frielingsdorf et al. |
| 5,224,473 A | 7/1993 | Bloomfield |
| 5,307,793 A | 5/1994 | Brumley et al. |
| 5,463,693 A | 10/1995 | Becker et al. |
| 5,503,141 A | 4/1996 | Kettl et al. |
| 5,572,990 A | 11/1996 | Berlin |
| 5,626,132 A | 5/1997 | Miller et al. |
| 5,802,198 A | 9/1998 | Beavers et al. |
| 5,895,537 A | 4/1999 | Campbell |
| 6,164,277 A | 12/2000 | Merideth |
| 6,174,278 B1 | 1/2001 | Jaeger et al. |
| D441,353 S | 5/2001 | Sun |
| 6,382,206 B1 | 5/2002 | Palazzotto et al. |
| 6,606,388 B1 * | 8/2003 | Townsend et al. ............. 381/17 |
| 6,950,682 B2 | 9/2005 | Atsumi et al. |
| 6,997,178 B1 | 2/2006 | Reynaud |
| 7,394,905 B2 | 7/2008 | Miller et al. |
| 7,457,427 B2 | 11/2008 | Birli et al. |
| 7,493,899 B2 | 2/2009 | Davies |
| 7,639,824 B2 | 12/2009 | Franzen |
| 2001/0012373 A1 | 8/2001 | Graumann |
| 2002/0110252 A1 | 8/2002 | Liu |
| 2003/0016211 A1 | 1/2003 | Woolley |
| 2005/0069160 A1 | 3/2005 | Kehoe |
| 2005/0256594 A1 | 11/2005 | Wong et al. |
| 2006/0126886 A1 | 6/2006 | Combest |
| 2007/0165885 A1 | 7/2007 | Chou |
| 2009/0007596 A1 * | 1/2009 | Goldstein et al. ............. 63/1.11 |
| 2009/0111527 A1 | 4/2009 | Richardson et al. |
| 2009/0205662 A1 | 8/2009 | Kwok et al. |
| 2010/0324374 A1 | 12/2010 | Choi et al. |
| 2011/0051944 A1 | 3/2011 | Kirkpatrick |
| 2011/0125060 A1 | 5/2011 | Telfort et al. |
| 2012/0206384 A1 | 8/2012 | Marsden et al. |

* cited by examiner

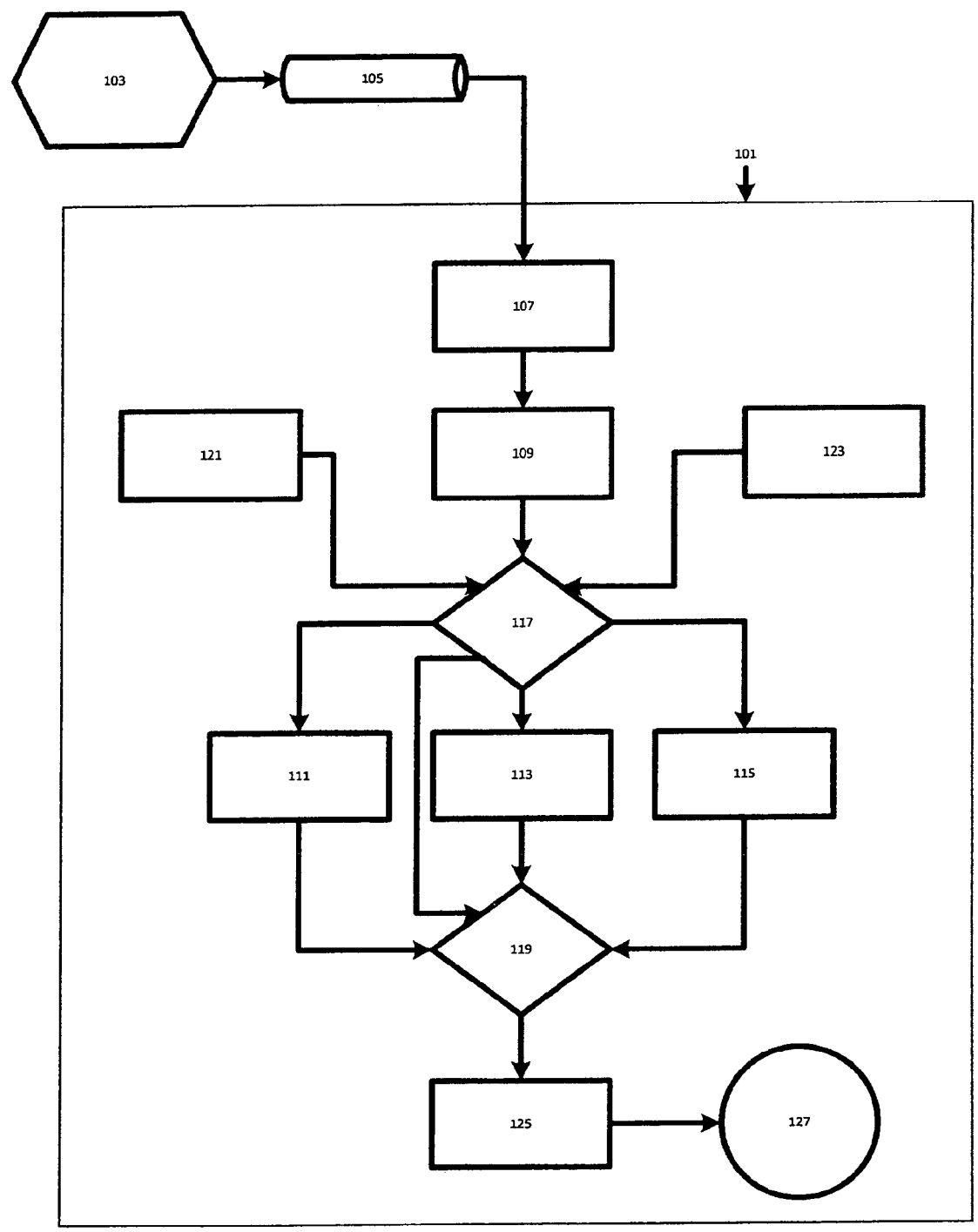

COMMUNICATION AND SPEECH ENHANCEMENT SYSTEM

CROSS-REFERENCE TO RELATED APPLICATION

This patent document claims the benefit of U.S. Provisional Patent Application No. 61/744,385, filed on Sep. 24, 2012, as well as U.S. Provisional Patent Application No. 61/849,326, filed on Jan. 23, 2013, both in the names of John Hamilton et al. The entire disclosures of each of these commonly owned patent applications are expressly incorporated herein by reference.

STATEMENT REGARDING FEDERALLY SPONSORED RESEARCH

None.

BACKGROUND OF THE INVENTION

1. Field of the Invention

The instant invention relates to the field of clinical communication with patients. More specifically the invention features a system which allows verbal communication by persons wearing respiratory assistance apparatus, the system featuring a user interface and/or an audio output transducer that is easily cleaned and sanitized.

2. Discussion of Related Art

Just in the medical field alone, there are a number of different positive pressure ventilators. Among the most common are C-PAP, Bi-PAP and A-PAP. C-PAP stands for "Continuous Positive Airway Pressure". This ventilator provides the patient with a constant positive air pressure to keep the patient's airways open and prevent obstruction due to muscle relaxation. Bi-PAP, or "Bilevel Positive Airway Pressure", deliver two pressure levels instead of one, and which pressure levels are synchronized to assist in the inhalation and exhalation processes. A-PAP is a species of C-PAP apparatus that automatically titrates a patient's pressure.

There are a number of situations in which a person needs to wear a respirator, either of the mask or the full-face variety, in order to be able to breathe adequately and properly. An almost universal problem with such respirators is that it makes normal verbal communication difficult, as the mask portion of the respirator tends to muffle the sound. In addition, a number of such respirators are "active" in the sense that they assist in inhalation and exhalation of air or oxygen, e.g., by means of a pump. The pumped air can make a "whooshing" sound that competes with the patient's speech, thus adding to the difficulty for the listener.

One potential solution to this problem is to introduce electronics, with electrically-powered transducers such as microphones and speakers. There are existing systems for communications with persons wearing respirators and face masks. Two examples include fire-fighting and scuba communication devices which allow persons wearing such equipment to communicate verbally with remote persons. These systems typically involve communication with remote persons through a wireless link or umbilical cable to remote devices. Thus, these systems are not arranged for general listening, but instead require a receiver for each person who wishes to hear the communication. Further, such a system requires a cable connection or some form of radio transmission.

Another related system is the one that physicist Stephen Hawking uses to verbalize with others. But this system is not processing his actual speech, but instead is synthesizing speech based on a non-speech input from him. As such, the "speech" sounds unnatural, and fails to convey the tonal qualities and emotions of the speaker.

Another issue that arises in the health care setting, however, is sterilization. Clinical and medical applications require equipment to be cleaned between uses. Traditional control inputs on medical devices employ knobs, buttons, and switches that inherently possess small openings, overhangs, ridges, and other surfaces that may capture contaminants, and are not easily cleansed. Typical practice requires devices to be either enclosed with a sterile, disposable covering during use, or to be disassembled and hand cleaned by technical specialists. The drawbacks of a sterile cover are that it must possess some type of opening to accommodate electrical leads while maintaining a sterile condition. In addition, the cover material naturally inhibits accurate view of indicators and displays, and the texture and slick nature of transparent cover materials reduces accurate manipulation of control knobs and switches. Manual cleaning and disassembly by skilled technicians adds substantially to the operational cost of equipment, and exposes service personnel to potentially infections disease.

Traditional audio output devices consist of an electromechanical transducer (speaker), inside of an enclosure which possesses an opening through which the sound may propagate. These openings may be covered with a perforated rigid material, a screen, a permeable cloth/textile, or membrane/laminate sheet of sufficiently thin cross section to allow resonation in harmony with the transducer thereby allowing sound to exit the enclosure.

In cases of perforated, screen, or textile coverings, contaminants are permitted to enter the perforations or fabric, thereby creating an unsanitary condition that is not easily cleaned. In cases of the thin membrane covering; while the membrane surface maintains advantageous non-porous properties, the arrangement suffers audio output attenuation, signal degradation, and distortion due to the air gap between the speaker diaphragm and the membrane, as well as from the mechanical properties of the membrane itself which acts as a semi-rigid passive radiator.

This new device addresses both the issues related to control inputs and audio output.

SUMMARY OF THE INVENTION

The present invention features a communication system for persons wearing respiratory apparatus. The system provides the means for normal verbal communication that is otherwise impossible when wearing respiratory apparatus. In the medical treatment setting, communication can occur in the same room with the patient and provides patients the ability to communicate verbally with doctors, staff, and visitors.

In accordance with the present invention, a transducer is affixed to the patient to convert audible vibrations to an electrical signal having audio range frequencies. The transducer provides this electrical signal to electronic modules which modify and enhance the signal. The enhanced signal is then amplified and converted back into an audible sound of speech by means of another transducer.

The various electronic modules are controlled by a user of the system or device by means of a user interface. To accommodate user input, the device possesses at least one external surface of the user interface having a dielectric constant favorable to transmission of a small electric field suitable for use with capacitive touch sensor circuits on the reverse side. These circuits allow the user to provide an input simply by placing a finger over the sensor area. The external surface is constructed of a sheet of material such as glass, acrylic, carbon fiber, fiberglass, plastic, combination laminate, or other suitably strong, smooth material. This surface, being smooth and free of buttons, switches, openings, overhangs, ridges, or crevices, allows for easy disinfecting with standard cleaning solutions and by non-specialist personnel.

The audio output portion of the system or device is also designed with ease of cleaning and sterilizing in mind. In particular, and rather than use a loudspeaker as the diaphragm for the second transducer, audio output is provided by a solid surface exciter such as by means of those known in the art, for example, as disclosed in U.S. Pat. No. 7,386,137.

In one embodiment, the solid surface exciter is affixed to the inside surface of the surface material thereby employing the surface material as the transducer diaphragm. By placing the user input devices on the same surface area as the audio output device, overall device size may be reduced.

Additional user feedback may be provided though haptics which employs a haptic motor producing tactile feedback through the surface material to acknowledge and confirm a user input.

Thus, in one of its embodiments, this new device addresses both the issues related to control inputs and audio output through a novel application combining capacitive input detection and a solid surface transducer.

Additional features such as wireless signalling and noise cancellation will also be described.

BRIEF DESCRIPTION OF THE FIGURES

The FIGURE is a schematic block diagram showing the conversion of sound such as speech into and out of an audio signal, and the path of that signal as it is processed.

DETAILED DESCRIPTION OF THE INVENTION

The instant invention pertains to communication systems for persons wearing respiratory apparatus that otherwise would prevent verbal communication. One aspect of the invention pertains to medical patients who wear such respirators to help them breathe. In this aspect of the invention, one embodiment of the invention can be a stand-alone system that can be used with existing respirator equipment such as C-PAP, A-PAP and Bi-PAP. Another embodiment of the system has the communications system integrated or built into the respirator equipment ("machine").

The communication and speech enhancement system of the instant invention features a first transducer such as a microphone whose electrical signal output is connected by wire or wirelessly to a signal processor to enhance intelligibility. Such connection may be referred to as an "interface". Operating power for the system is electrical in nature and may be supplied by local line voltage or batteries, or line voltage with battery backup.

The system specifically modifies the signal to produce intelligible speech at sufficient listening levels for clinical applications. The output of the signal processing is a "line level" electrical signal at audio frequencies. This electrical signal may then serve as the audio input for an amplifier for a second transducer the audio output transducer.

The first transducer is arranged to be removably attached to the human wearer on the throat at or near the larynx ("voice box"). In one embodiment, the means for attachment is a strap which may be elastic and which may feature fasteners known in the art such as VELCRO hook-and-loop attachment system. In an alternate embodiment, sometimes referred to as "the self-stick attachment method", the first transducer may be integrated with a sterile fabric swatch or bandage incorporating a self-adhesive and applied directly to the patient in a manner similar to an EKG sensor. In a second alternate embodiment, the first transducer may be mounted in the respiratory mask component of the respiratory machine. This first transducer may be hermetically sealed to allow cleaning and disinfecting with liquid disinfectants. In each of these embodiments, the first transducer, e.g., microphone, may be cylindrically shaped, and may be mounted in a ring-shaped housing, which is then attached to the strap, fabric swatch/bandage or respirator. The housing may feature one or more protrusions that extend from the circumference into the interior space defined by the ring, the protrusions serving to prevent the cylindrically shaped first transducer from extending too far into the housing. In this way, the first transducer can be maintained at a desired distance from the larynx.

From the interface, the electrical signal travels to the speech processing unit, which here is termed the "Speech Enclosure". The overall system of the instant invention may optionally include a main amplifier and the second transducer, and these two devices may also be housed in the speech enclosure.

At a minimum, the audio processing unit features a high pass filter to remove bass frequencies below a certain threshold frequency. Functionally, this action eliminates or at least greatly reduces the very low frequencies associated with impacts and physical contact with the first transducer.

The audio processing unit optionally may feature other components for additional specific processing of the speech. These other components include volume and tone controls, a dynamics processor, an equalization circuit, a feedback suppressor, and processing sequence controls.

The volume and tone controls are similar in function to those found on common audio equipment such as a radio, television or portable audio equipment such as a portable, tape, CD, or MP3 player, or "boombox".

The dynamics processor controls the dynamic range of the speech, that is, the range from quiet to loud, that is, the intensity range. Here, this typically means compressing, or "limiting the headroom" of the very loud sounds. Optionally, the dynamics processor may also expand or amplify the very soft or quiet sounds.

The equalization circuit is similar to that found on better quality stereo systems. Here, instead of having a pair of controls for "bass" and "treble", the audio spectrum is broken into a plurality such as half a dozen or more segments or "channels", each of which can be controlled in terms of volume (enhanced or suppressed) independently of the other channels.

The feedback suppressor is designed to do exactly that—suppress audio feedback. Feedback typically manifests itself as a high pitched squeal or howl, and results from the output of a loudspeaker re-entering the microphone from which the output originated in excess quantities. Feedback is most likely to occur when the microphone is too close or aimed to much toward the loudspeaker. The feedback suppressor works by providing a time-based delay, a notch-type filter, or both.

The processing sequence controls provides the user of the system with control over which of the optional components of the speech processing unit are activated, and in which order. The order in which the audio signal is processed affects the signal. Thus, the user is able to experiment with different signal paths to obtain the best results, for example, in terms of speech intelligibility.

The invention will now be further described with reference to the FIGURE, which illustrates one embodiment of the invention. Referring to this FIGURE, the audio processing unit, main amplifier and audio output transducer are housed in a single "speech enclosure", as indicated by the large box 101. Outside of this box to indicate its physical separateness is the first transducer 103 such as an audio microphone. The first transducer produces an electrical signal that is connected with wires or wirelessly to the speech enclosure 101 through the interface unit 105.

Once inside the speech enclosure 101, the signal is first amplified, for example, to "line level" by means of a high gain pre-amp 107. Next, the signal passes through the high pass filter 109. From there, the signal may pass through one or more other processors such as the dynamics processor 111, the equalization circuit 113 and/or the feedback suppressor 115. The signal path processor 117 and signal return path processor 119, as activated by the processing sequence controls 121, a user interface device, determines which of these other signal processors the signal passes through, and in what order. This speech enclosure also features the volume/tone control 123. After completing signal processing, the signal passes through the main audio amplifier 125 and into the second transducer, which may be a loudspeaker 127. Here, the audio signal is converted into pressure pulses of air that are heard as sound by the ear and brain of the human body.

In a third alternate embodiment of the invention, a given processing element may be duplicated, as long as the duplicate is not placed immediately adjacent the original processing element. For example, it may be desirable for the audio processing unit to contain two equalizer circuits, with the dynamics processor element placed between them.

In a fourth alternate embodiment of the invention, the audio signal processing could employ negative feedback in a desirable manner. Specifically, one could invert a portion of the output signal from the audio processing unit, i.e., make its polarity negative, filter out selected frequencies or dynamics from the signal, and the insert it back into the input stage of the audio processing unit. Because of the inverted polarity, the balance of the original and inverted signals cancel each other out, leaving the selected frequencies or dynamics from the original signal to pass through.

Wireless Aspect

In a second major aspect of the invention, instead of being routed to the interface/speech enclosure, the output of the first transducer may be sent wirelessly instead to a receiving device such as a Personal Digital Assistant (FDA) or cell phone. Specifically, the microphone housing may incorporate a battery powered radio transmitter. This transmitter is electrically connected to the first transducer (patient microphone) and employed to wireless)), conduct the electrical signal from the first transducer to the FDA, cell phone, or other device with a compatible radio receiver, (receiving device). The received signal may receive processing similar to that provided by the "Signal Processor" in the "Speech Enclosure" through a software application running on the receiving device. This embodiment allows the receiving device to output an amplified and processed signal from its onboard output speaker as well as to facilitate the ability for the wearer to conduct telephone calls, and for the signal to be integrated with other application software such as a voice recorder, speech recognition software, or environmental control systems. A variation on this embodiment includes an ear-piece speaker that is connected either by wire or wirelessly to either the first transducer/radio assembly or FDA. This ear-piece speaker attaches to the patient's ear and emits an audio signal which is received electrically from the FDA or cell phone, for example the voice of the second party in a phone call, or the audio from a software application, movie, or game.

In a fifth alternate embodiment of the invention that is at least somewhat related to the fourth alternate embodiment, and which can be used with either the first or second major aspect of the invention, the audio signal processing could employ noise cancellation technology in a desirable manner. Specifically, additional input transducers, microphones, may be employed to increase the signal-to-noise ratio and to reduce acoustic feedback. These additional input transducers capture ambient sounds in the local area of the patient. These transducers may be integrated into the "Speech Box" enclosure, integrated with the first transducer (patient microphone) assembly, or placed separately in the local environment. The electrical output signals from the additional transducers are connected by wire or wirelessly to the "Signal Processor". These signals may receive individual processing similar to that afforded the signal from transducer and be applied in whole or in part, inverted or non inverted to the electrical signal from the first transducer to improve the signal-to-noise ratio by removing any ambient sound or acoustic feedback.

One issue with so-called throat transducers is that the mid-high and high frequencies of speech are often lacking. Accordingly, in another embodiment of the instant invention, the signal processing unit may also feature a "sibilance enhancer/synthesizer" and/or an aural exciter to add high frequency "hiss" and the mid-high frequencies of the speech, respectively, to the audio signal.

The interface provides the means by which the user of the present device may adjust the audio output such that the speech from the patient is intelligible. Another embodiment of the present invention provides at least one external surface for the interface (or "user interface") that is easily cleaned and sanitized. More specifically, this external surface of the speech enclosure may be constructed of a sheet of material such as glass, acrylic, carbon fiber, fiberglass, plastic, combination laminate, or other suitably strong, smooth material. This surface, being smooth and free of buttons, switches, openings, overhangs, ridges, or crevices, allows for easy disinfecting with standard cleaning solutions and by non-specialist personnel.

To accommodate user input, the surface material possesses a dielectric constant favorable to transmission of a small electric field suitable for use with capacitive touch sensor circuits on the reverse side. These circuits allow the user to provide an input simply by placing a finger over the sensor area. The surface material maintains a thickness and resiliency commensurate with use in the applicable commercial service. This material may be imprinted with graphics and icons indicating location and function of capacitive input controls. When clear surface material is employed the graphics may be imprinted on the reverse side, and interior illumination may be provided to highlight input control areas, or to display information and status to users. Display devices include LEDs, incandescent lamps, LCD, LED, TFT, oLED displays, and other user interface graphic devices. Illumination may change state (on/off), intensity, or color, to indicate receipt of a user input by providing a visual feedback. The capacitive sensor circuitry is affixed to the inside of the surface material and is connected to the control circuitry of the device through an electrical connection.

In addition, and in another embodiment of the present invention, the device provides an audio output transducer (the "second transducer") that also may be readily and easily cleaned and sanitized. Specifically, such audio output is provided by means of a solid surface exciter such as those known in the art, for example, as disclosed in U.S. Pat. No. 7,386, 137, the entire disclosure of which is herein incorporated by reference.

The solid surface of the solid surface exciter may be a different surface than that for the user interface, but in one embodiment, it is the same surface, that is, the user interface doubles in function as the audio output surface.

In this embodiment, the second transducer is affixed to the inside surface of the surface material thereby employing the surface material as the transducer diaphragm. The lack of an air gap between the exciter motor and the surface material eliminates compression distortion, attenuation, and other signal degradation suffered by speakers mounted behind membranes. Other advantages of the solid surface material exciter relate to efficiency and output amplitude. The device allows the entire surface material to act as an acoustic radiating surface, thereby providing a much greater surface area for acoustic wave generation than a traditional speaker which employs a much smaller surface area. The transducer is driven by any standard audio amplifier, and electrically appears as a traditional speaker in circuit design. The transducer is connected to the amplifier circuit with a flexible electrical lead that allows free motion of the transducer throughout the operational frequency range and amplitude desired.

The surface material is attached to the device enclosure in a method allowing a certain range of linear motion congruent with the direction of motion generated by the solid surface exciter. The attachment method of the surface material to the enclosure is optimized to allow the surface material to resonate at a frequency desirable for the application. The surface material is isolated from the enclosure by an appropriate durometer gasket which acts as an acoustic suspension and provides for the oscillating linear motion of the surface material while maintaining seal integrity against liquid and contaminant ingress. For example, for human speech output, a resonant frequency of approximately 2000 Hz may be desirable, whereas in a dog bark prevention device a much higher resonant frequency is needed. Resonant frequency is tuned through variation of the gasket shape and contact surface area as well as the selection of material. Low and high pass filters in the exciter driver circuitry can be employed to restrict exciter frequencies to the operational design parameters of the surface material and application requirements.

By placing the user input devices on the same surface area as the audio output device, overall device size may be reduced. Since both functionalities exist in the same area, size and cost savings may be achieved without a compromise in performance.

In another aspect of the present invention, additional user feedback may be provided though haptics which employs a haptic motor producing tactile feedback through the surface material to acknowledge and confirm a user input. The haptic motor is affixed to the inside surface of the surface material and connected to control and driver circuitry through an electrical lead. The frequency of the haptic signal is selected to be outside the operating frequency of the solid surface exciter to allow user discrimination between audio output and haptic feedback.

The capacitive touch sensors, illumination and display devices, and the haptic motor may be employed on a single surface, or on multiple surfaces.

INDUSTRIAL APPLICABILITY

Among the features and attributes of the present invention are:
  Exceptional sensitivity to allow even very weak patients to communicate
  Smooth surface(s) for the user interface and/or audio output transducer permit cleansing with liquid disinfactant
  Signal dynamics modulation to mitigate loud sounds such as coughing and transducer impact
  Elimination of sounds caused by air movement from respiratory devices
  Signal enhancement to provide intelligibility
  Signal conditioning to prevent audio feedback.
  Various controls to adjust signal processing to optimize signal conditioning for individual patients.
  Additional user tactile feedback via haptics
  System to have no interference or effect on respiratory equipment, masks, or pulmonary treatments
  Signal conditioning electrical architecture to allow changes in signal path through the various signal conditioning sections to provide flexibility in tuning and optimization to various patients
  Auxiliary interfaces to provide integration with existing patient monitoring systems.
  Auxiliary telephone interface provides muting control to provide for private communication
  Auxiliary headphones to listen to patient The instant speech enhancement system will be of immediate use to persons who are using machines to help them breathe such as C-PAP, A-PAP, and Bi-PAP. The instant speech enhancement system will also be of utility and therefore of interest in other situations such as in a work environment where a respiratory mask must be worn for protection against airborne contaminants.

Because of its ability to run on battery power, the instant communication and speech enhancement system is not tethered to AC "house current", but instead is highly portable. Thus, the system can be provided to ambulance, fire, police and other emergency first responders, to automobiles, to bicycles, to wheelchairs and power chairs, and to public transit system such as aircraft, trains including subway systems, buses and motor vehicles for hire such as taxis.

An artisan of ordinary skill will appreciate that various modifications may be made to the invention herein described without departing from the scope or spirit of the invention as defined in the appended claims.

What is claimed is:

1. A system for enhancing verbal communication of a wearer of a respiratory apparatus that degrades a quality of speech by a patient, said system comprising:
    a first transducer arranged to attach at or near a throat of the wearer of the respiratory apparatus, said transducer converting sound produced by the wearer into an electrical signal;
    a plurality of processing components configured to process said electrical signal to form a processed electrical signal capable of being reproduced into patient speech, wherein the plurality of processing components includes at least:
        a first processing component configured to filter out frequencies below a selected threshold frequency, and
        a second processing component; and
    a user interface including at least one control to receive input indicating a sequence in which the plurality of processing components process said electrical signal, such that a sound quality of the patient speech reproducible from the processed electrical signal is adjustable by a user via the user interface so as to improve intelligibility of the patient speech.

2. The system of claim 1, further comprising an auxiliary interface for controllably routing said processed electrical signal to at least one of a portable music player, a mobile telephone, a smartphone, or a personal computer selected from the group consisting of a desktop, a laptop and a tablet.

3. The system of claim 1, further comprising at least one amplifier to amplify said processed electrical signal, said amplification being sufficient to drive a second transducer to convert said processed electrical signal back into audible sound.

4. The system of claim 3, further comprising an auxiliary interface for controllably routing said amplified processed electrical signal to at least one of a loudspeaker, a pair of headphones, or an earphone.

5. The system of claim 3, further comprising a second transducer to convert said amplified electrical signal back into audible sound.

6. The system of claim 5, wherein said plurality of processing components and said amplifier and said second transducer are housed in a single enclosure.

7. The system of claim 6, wherein said enclosure is connected by at least one wire to said first transducer.

8. The system of claim 6, wherein said enclosure is connected wirelessly to said first transducer.

9. The system of claim 5,
wherein at least one of said user interface or said second transducer comprises a smooth surface amenable to cleaning and sterilizing with a liquid disinfectant agent.

10. The system of claim 9, wherein said smooth surface is constructed of at least one sheet of material selected from the group consisting of glass, acrylic, carbon fiber, fiberglass, and plastic.

11. The system of claim 9, wherein said user interface comprises at least one capacitive touch sensor circuit mounted on a surface opposite said smooth surface.

12. The system of claim 11, further comprising at least one of a graphic and an icon displayed on said smooth surface to indicate location and function of the at least one control, wherein the at least one control is a capacitive input control.

13. The system of claim 5, wherein said second transducer comprises at least one of a solid surface exciter or a loudspeaker.

14. The system of claim 5, further comprising a means for attenuating an ambient noise component of said audible sounds.

15. The system of claim 1, wherein said first transducer is arranged to be attached at or near the voice box by means of a detachable strap arranged to encircle a neck of the wearer of the respiratory apparatus.

16. The system of claim 1, wherein the plurality of processing components includes a dynamics processor.

17. The system of claim 1, wherein the plurality of processing components includes at least one equalization circuit to amplify or attenuate selected frequency bands.

18. The system of claim 1, wherein the plurality of processing components includes a feedback suppression element.

19. The system of claim 1, wherein the plurality of processing components includes at least one of volume or tone control.

20. The system of claim 1, further comprising signal processing via a negative feedback loop.

21. The system of claim 1, wherein said first transducer is hermetically sealed to allow cleaning and disinfecting with liquid disinfectants.

22. The system of claim 1, integrated into a piece of respiratory equipment selected from the group consisting of C-PAP, A-PAP and Bi-PAP.

23. The system of claim 1, further comprising:
a transmitter arranged to convert said electrical signal or processed electrical signal in to an electromagnetic wave, and further arranged to transmit said electromagnetic wave to a device capable of receiving, decoding and converting said electromagnetic wave back into a reconstituted electrical signal or a reconstituted processed electrical signal.

24. The system of claim 1, further comprising a ring-shaped mount for said first transducer, wherein said first transducer is generally cylindrically shaped, and is arranged to be mounted at or near the voice box by mounting said first transducer in said mount such that a longitudinal axis of said ring-shaped mount coincides with the longitudinal axis of said first transducer, and further wherein said mount comprises at least one protrusion extending from a circumference of said mount into a space defined by said ring-shaped mount, whereby said first transducer is prevented from excessive travel axially with respect to said mount.

25. The system of claim 1, wherein the plurality of processing components includes at least one of a sibilance enhancer or an aural exciter.

26. The method of claim 25, wherein the plurality of processing controls at least one of a dynamics processor, an equalization circuit, a feedback suppression element, a volume control, a tone control, a sibilance enhancer, a noise cancellation element, or an aural exciter.

27. A system for enhancing verbal communication of a wearer of a respiratory apparatus that degrades a quality of speech by a patient, said system comprising:
means for converting sound produced by the wearer of the respiratory apparatus into an electrical signal;
a plurality of processing components configured to process said electrical signal to form a processed electrical signal capable of being reproduced into patient speech;
means for receiving input indicating a sequence in which the plurality of processing components process said electrical signal;
means for converting said processed electrical signal into an electromagnetic wave; and
means for transmitting said electromagnetic wave to a device capable of converting said electromagnetic wave into audible sound conveying the patient speech, wherein a sound quality of the patient speech reproducible from the processed electrical signal is determined in part by the sequence in which the plurality of processing components process said electrical signal so as to improve intelligibility of the patient speech.

28. A method comprising:
converting, by a first transducer attached to a wearer of a respiratory apparatus that degrades a quality of speech by a patient, audible sounds produced by the wearer into an electrical signal;
processing, by a plurality of processing components, the electrical signal into a processed electrical signal capable of being reproduced into patient speech, wherein the plurality of processing components includes at least:
a first processing component configured to filter out frequencies below a selected threshold frequency; and
a second processing component; and
receiving, by a user interface including at least one control, input indicating a sequence in which the plurality of processing components process said electrical signal, such that a sound quality of the patient speech reproducible from the processed electrical signal is adjustable by a user via the user interface so as to improve intelligibility of the patient speech.

* * * * *